(12) United States Patent
Murakami

(10) Patent No.: US 6,181,979 B1
(45) Date of Patent: Jan. 30, 2001

(54) MEDICATION PROCESSING SYSTEM

(75) Inventor: Takaaki Murakami, Toyonaka (JP)

(73) Assignee: Kabushiki Kaisha Yuyama Seisakusho, Oaska (JP)

( * ) Notice: Under 35 U.S.C. 154(b), the term of this patent shall be extended for 0 days.

(21) Appl. No.: 09/005,667

(22) Filed: Jan. 12, 1998

(30) Foreign Application Priority Data

Jan. 13, 1997 (JP) ................................................. 9-004061

(51) Int. Cl.$^7$ ..................................................... G06F 7/00
(52) U.S. Cl. .............................................. 700/216; 705/8
(58) Field of Search ............................ 700/95, 115, 111, 700/108, 215, 216, 218, 242; 705/8, 9

(56) References Cited

U.S. PATENT DOCUMENTS

| | | | |
|---|---|---|---|
| 5,208,762 | * 5/1993 | Charhut et al. | 364/478 |
| 5,597,995 | * 1/1997 | Williams et al. | 235/375 |
| 5,604,692 | * 2/1997 | Yuyama | 364/788 |
| 5,648,751 | * 7/1997 | Yuyama et al. | 340/309.15 |
| 5,907,493 | * 5/1999 | Boyer et al. | 364/479.01 |
| 5,988,858 | * 11/1999 | Yuyama et al. | 364/478 |

\* cited by examiner

Primary Examiner—William Grant
Assistant Examiner—Zoila Cabrera
(74) Attorney, Agent, or Firm—Wenderoth, Lind & Ponack, L.L.P.

(57) ABSTRACT

A drug preparation system which can indicate which drug processing or inspection station or stations are busy so that drugs can be prepared in an optimum way. Patient data recorded on prescriptions received at a pharmacy reception is entered into a host computer through an input device. On command of the host computer, patient data are transferred to respective drug processing units. Each processing unit enters time data including drug preparation completion time into trays with a memory function for collecting drugs prepared. The drugs collected in each tray are inspected and sent to a drug pickup window, where the time data are transferred to a data processing unit. Based on the transferred data, a total processing time in each station is displayed on a display.

16 Claims, 12 Drawing Sheets

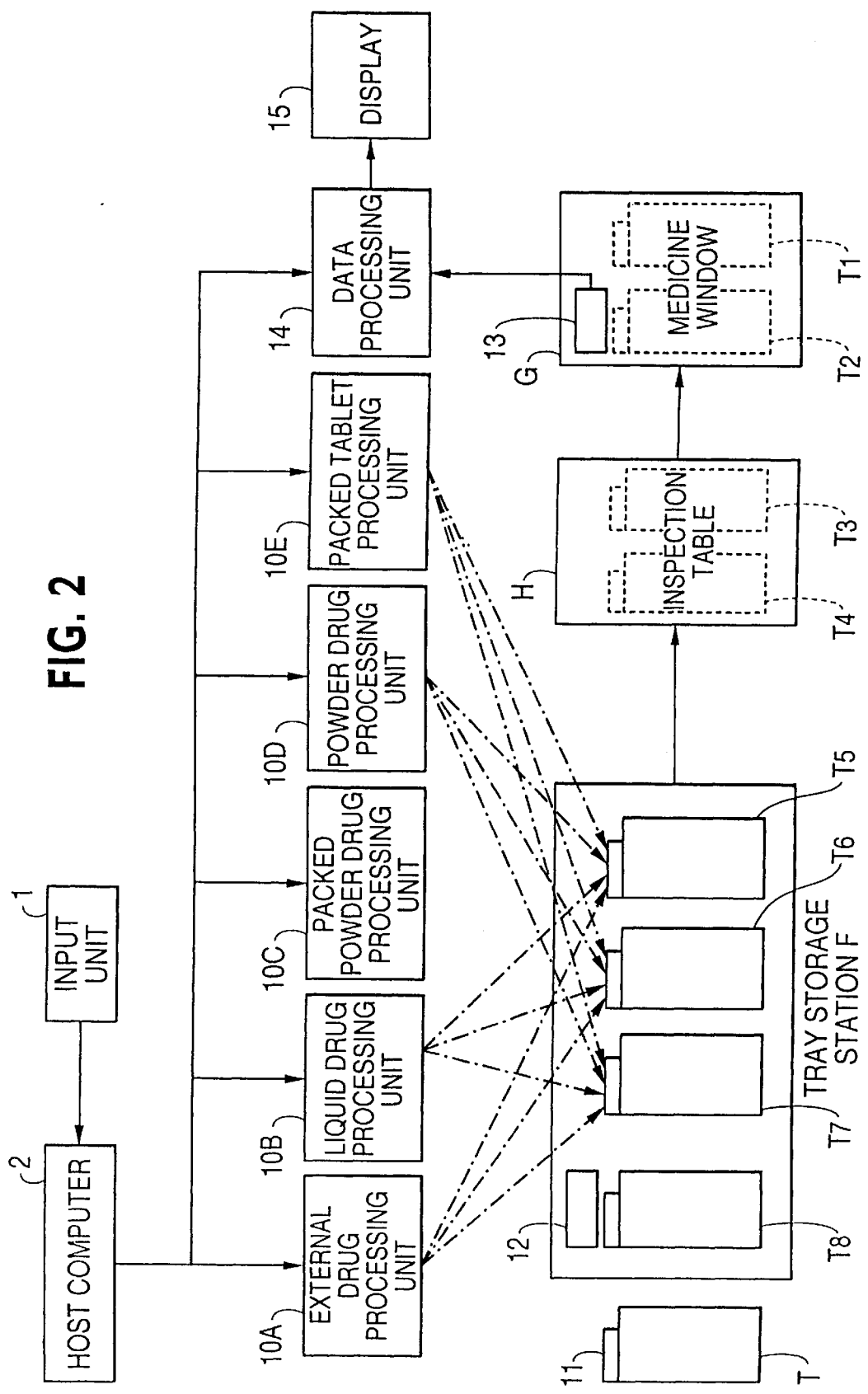

FIG. 6

| Administration indication system ver4.20.02  19 / /  10:45:05 |
|---|

Daily chart (for time range)   Date   , 1998

| Time range | Prescription received | Processing time (in min) | | | Prescription issued | Prescription waiting |
|---|---|---|---|---|---|---|
| | | Max | Average | Min | | |
| 8:30 ~ 8:59 | | | | | | |
| 9:00 ~ 9:29 | | | | | | |
| 9:30 ~ 9:59 | | | | | | |
| 10:00 ~ 10:29 | | | | | | |
| 10:30 ~ 10:59 | | | | | | |
| 11:00 ~ 11:29 | | | | | | |
| 11:30 ~ 11:59 | | | | | | |
| 12:00 ~ 12:29 | | | | | | |
| 12:30 ~ 12:59 | | | | | | |
| 13:00 ~ 13:29 | | | | | | |
| 13:30 ~ 13:59 | | | | | | |
| 14:00 ~ 14:29 | | | | | | |
| 14:30 ~ 14:59 | | | | | | |
| 15:00 ~ 15:29 | | | | | | |
| 15:30 ~ 15:59 | | | | | | |
| 16:00 ~ 16:29 | | | | | | |
| 16:30 ~ 16:59 | | | | | | |
| Total | | | | | | |

[ ] [f 2] [ ] [ ] [ ] [f 6] [f 7] [f 8] [f 9] [ ]

Printing   Date  Yesterday              Index
                       Tomorrow

Daily chart (Graph of processing time for each time range and each drug kind)

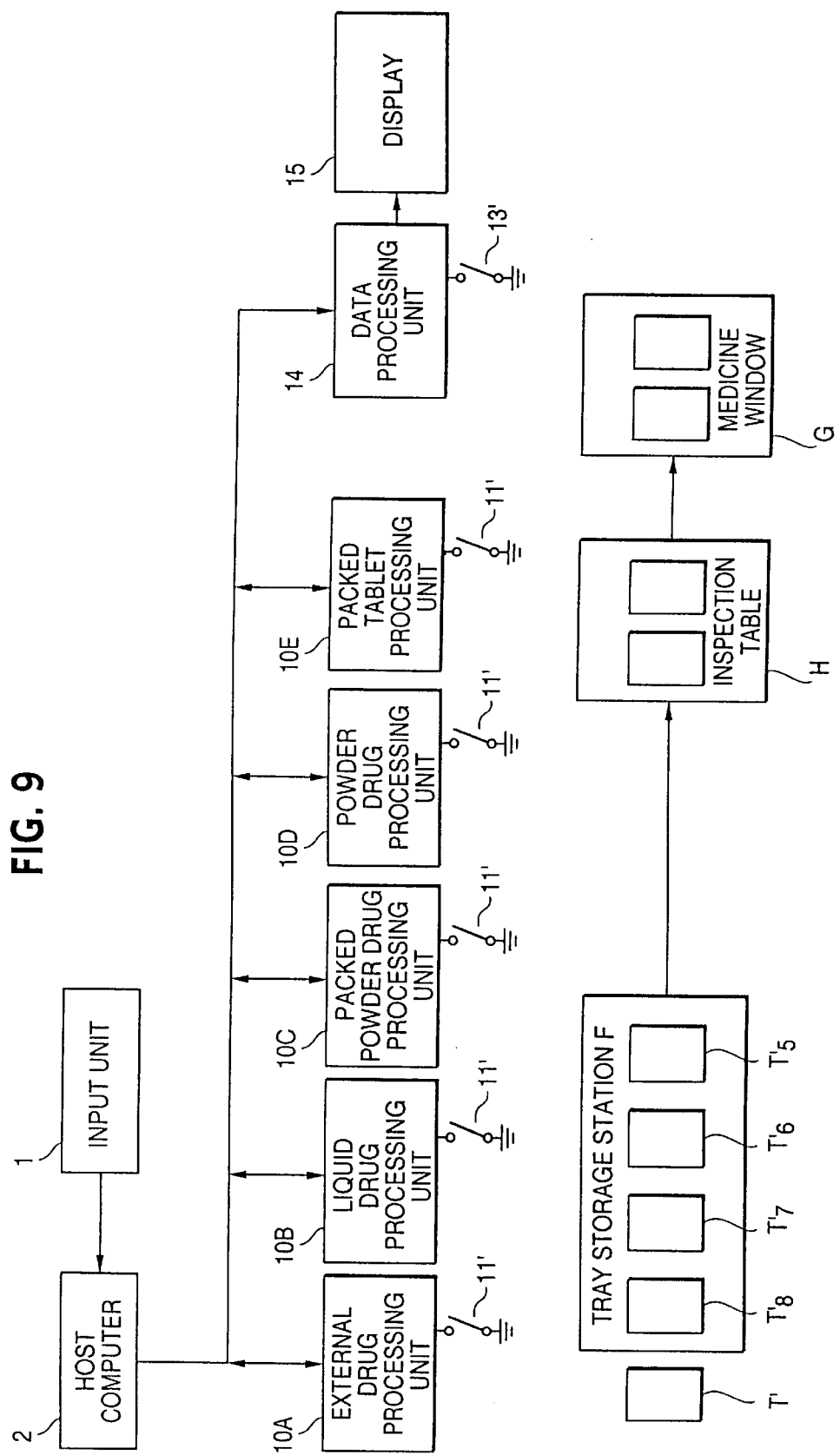

MEDICATION PROCESSING SYSTEM

BACKGROUND OF THE INVENTION

This invention relates to a medication processing system for use in a pharmacy in e.g. a hospital for prescribing and inspecting medications and gathering data on e.g. the processing time for each drug type at each processing station and processing the thus gathered data.

In a hospital pharmacy, when a pharmacist receives prescriptions or prescribing instructions, he selects drugs designated in the prescriptions from among a stock of medications including powdered drugs, tablets, external drugs and liquid drugs, prepares them, and hands the thus prepared drugs to patients. Workload for such drug preparations is increasing at a rapid pace with an increase in the kinds of drugs needed, resulting partly from sophistication of modern medicine and partly from an increasing number of departments due to fractionization. Thus, it is desired now, more than ever before, to prepare drugs efficiently and hand them to waiting patients as quickly as possible.

To prepare drugs efficiently, various devices have been developed and actually used. Such devices include tablet packaging machines which can package tablets for each dose, powder drug packaging machines for packaging a powdered drug for each dose, and drug conveyor means.

Apart from these drug preparation devices, unexamined Japanese utility model publication 63-139643 discloses a display device for displaying a drug preparation procedure. This device lets patients waiting for drugs know how soon they can receive their drugs. Specifically, this device indicates on a display panel in which stage is the drug preparation for each patient. This device also has a monitoring unit for monitoring the above information so that drugs for patients who have been waiting longer are prepared with priority.

Although such conventional arrangements enable the individual drug processing and inspecting units to operate with greater efficiency, they cannot necessarily shorten the entire drug processing time in an optimum way. For example, if a large quantity of powdered drugs have to be prepared in a given unit time range, it is impossible to sufficiently shorten the entire drug processing time even if the tablet processing unit can prepare tablets with greater efficiency.

But such a thing often happens. That is, in a given time range of one day or at a given time of one year, it may be necessary to prepare exceedingly larger quantities of drugs in a certain drug processing unit than in other drug processing units. Therefore, to improve the entire drug processing efficiency, it is necessary to get information on the workload on each drug processing unit in each unit time range. In the conventional systems, it is impossible to get such information.

The display device disclosed in the above utility model publication shows simply which type or types of drugs for each patient are not yet processed on the display panel and the monitor. It can not show which drug processing or inspecting station is heavily burdened with a workload.

That is, this device can simply estimate the waiting time for each patient and make it possible to process drugs for patients waiting longer with priority. It cannot tell which processing or inspecting station is currently the busiest.

This invention has been made to solve these problems of the conventional medication processing systems, and its object is to provide a medication processing system having a control unit for gathering and processing data on the processing time in the respective drug processing units and patient data and displaying the thus processed data on a display so that more pharmacy personnel can be distributed to the busiest station.

SUMMARY OF THE INVENTION

According to this invention, there is provided a medication processing system comprising a plurality of drug processing units for preparing medications according to data indicated on prescriptions including the kinds and quantity of medications and patient names or codes. The drug processing units are provided around a carrier storage area for temporarily storing drug carriers, and a control unit is provided for storing data on drug preparation starting and completion times and processing times in the respective drug processing units and a drug inspection station and calculating the total processing time in each of the drug processing units and the drug inspection station during each time range, and for each kind of drugs.

When patient data are delivered to each drug processing unit, drug preparation starts in each unit. When the patient data and the data on the drug preparation starting and completion hours are entered into the control unit, the control unit processes these data.

Specifically, the control unit calculates the total processing time period in each of the drug processing and drug inspection stations and the grand total of such total processing time periods.

Such data on total processing time periods may be shown on a display so that pharmacists can instantly see the processing time in each station in each unit time zone. Also, standard data or pattern, for each station for the whole day, may be calculated beforehand so that pharmacists can easily tell which station is the busiest by comparing the actual pattern with the standard pattern.

Other features and objects of the present invention will become apparent from the following description made with reference to the accompanying drawings, in which:

BRIEF DESCRIPTION OF THE DRAWINGS

FIG. 2 is a block diagram of a drug processing system;

FIG. 6 shows data shown on a display;

FIG. 9 is a block diagram of a drug processing system of a second embodiment.

DETAILED DESCRIPTION OF THE PREFERRED EMBODIMENT

Figure 1:
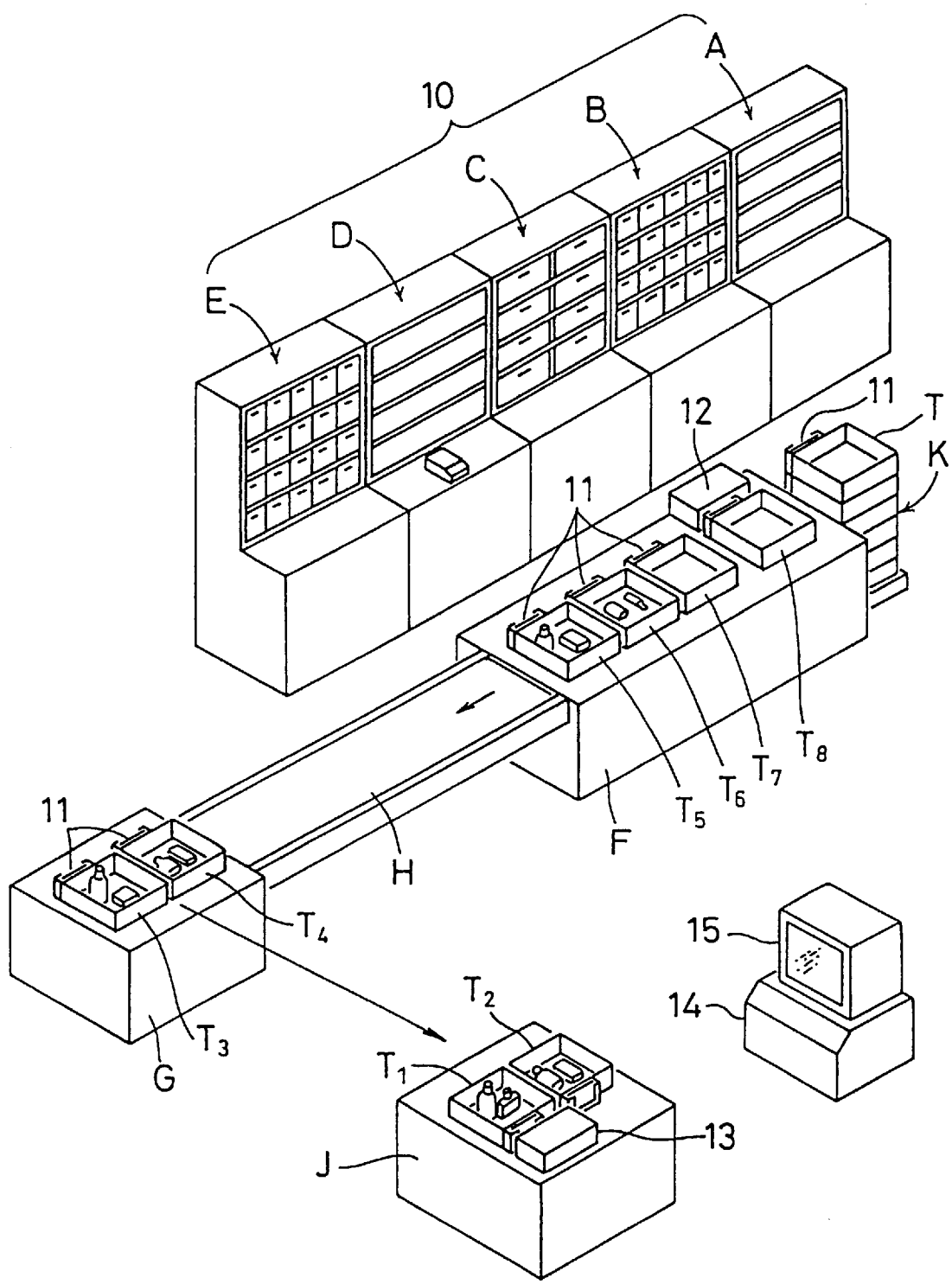
FIG. 1 is a perspective view of a drug processing unit.

Now referring to the drawings, the embodiments of this invention are described. FIG. 1 is a perspective view of a medication processing system according to this invention. The illustrated system collects prescribed drugs in trays carrying memories which can store data on drug processing time and other data on drug preparations. The thus collected drugs are inspected and handed to patients.

This system has a drug processing unit 10 which comprises a powdered drug processing unit 10A, liquid drug processing unit 10B, packed powder processing unit 10C, tablet processing unit 10D and external drug processing unit 10E. While not shown, the processing unit 10 may further include a packed tablet processing unit and a drug bag processing unit. Each processing unit has a display CRT, not shown, for displaying the names or codes of drugs to be processed in the respective processing unit.

The processing unit 10 may be of any known type. For example, the tablet processing unit 10D may be of a type capable of automatically selecting a plurality of kinds of tablets and packaging them in one bag. The powder drug processing unit 10A may be of a type capable of separately packaging a plurality of kinds of powdered drugs prepared by a pharmacist in a predetermined amount each.

The processing units may be arranged side by side in a line as shown in FIG. 1 or in any other way. A tray storage area F (table) is provided opposite the processing units. An inspection table G is provided slightly apart from the area F and is connected to the area F through a short conveyor H. Another table J sits at the drug delivery window on which are placed drugs that are ready to be handed to patients. A plurality of trays T are stacked at a tray storage station K. Each tray T has an electronic data memory 11.

A plurality of trays T (such as trays T5–T8) can be placed on the tray storage area F at a time. Provided at upstream end of the area F is a data transmitter 12 for entering data in a non-contact manner. The transmitter 12 transmits patient data in the form of light signals into the memory 11 of each tray in the manner to be described later. Drugs for each patient are collected in one tray T1, T2, . . . and delivered to the inspection table G.

A pharmacist inspects the drugs in each tray placed on the inspection table G. After inspection, trays (such as trays T1 and T2) are hand-carried onto the table J. Data on the drugs in the trays T1 and T2 placed on the table are read by a non-contact type receiver 13 on the table J for data processing and analysis by a data processing unit 14, which is a personal computer. The results of processing or analysis are shown on a display (CRT) 15.

FIG. 2 is a block diagram of the medication processing system. When prescriptions are received, a pharmacy receptionist enters patient data (drug data) on the prescriptions into a host computer 2 through an input unit 1, together with reception numbers and patients' names or codes. The host computer 2 transmits this data to the processing units concerned to indicate these data on the displays (not shown) of the respective processing units so that pharmacists can prepare necessary drugs.

Figure 3A:
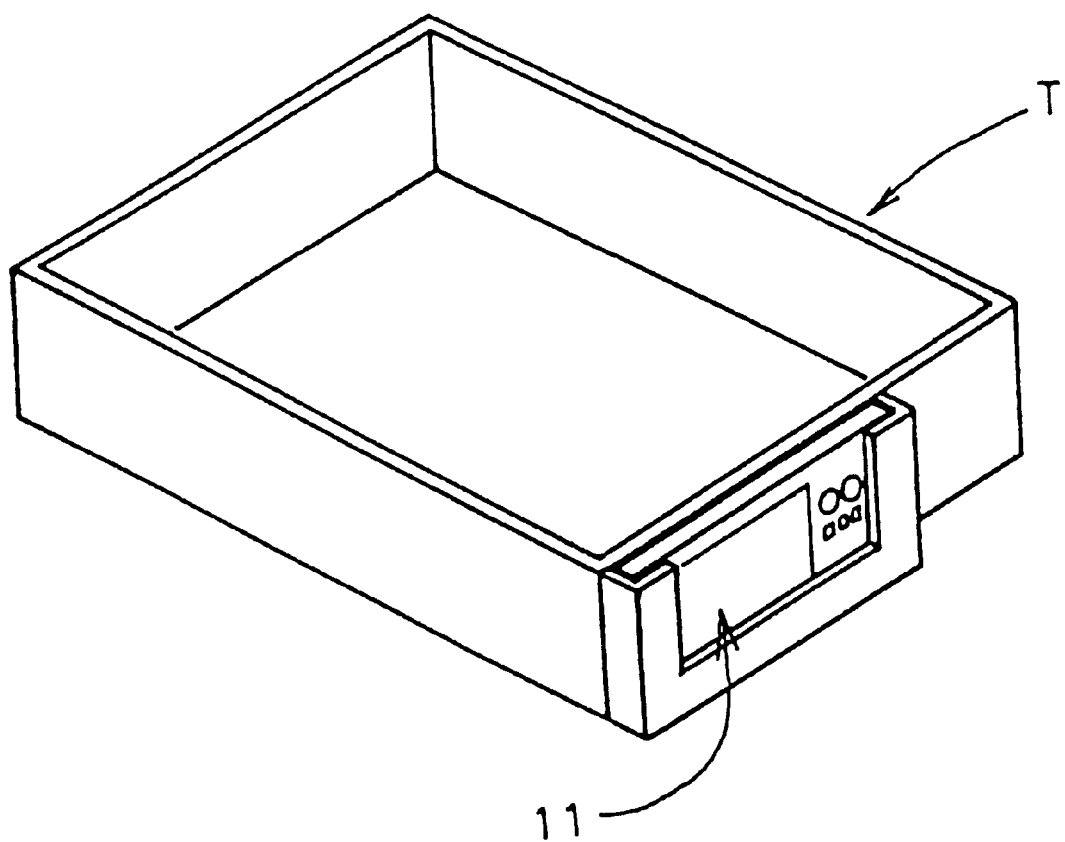
FIG. 3A is a perspective view of a tray with a memory.

FIG. 3A shows a tray having a data memory. The illustrated tray is disclosed in Japanese patent application 6-272037. For details of this tray, reference should be made to this document. Here, the tray is discussed only briefly.

The tray T is a shallow, open-topped box of a size suitable for hand-carrying with drugs put therein. The tray T may be made of wood, paper, metal or whatever provided it is sufficiently lightweight. Its shape is also not limited to the illustrated open-topped box shape. It may also have a cover or a side opening.

Figure 3B:
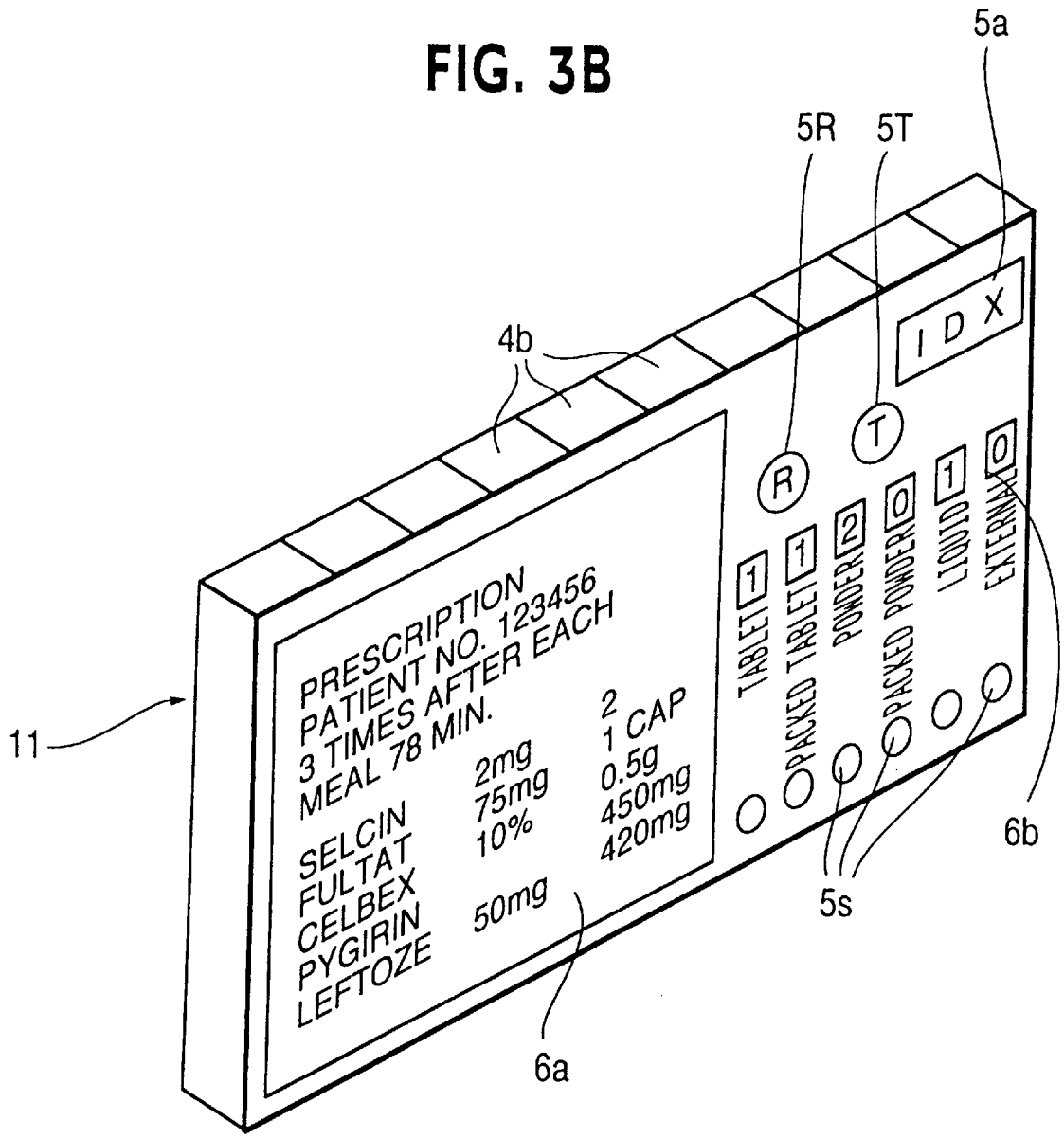
FIG. 3B is a perspective view of the memory of the tray of FIG. 3A.

A data memory 11 shown in FIG. 3B is detachably mounted to one side of the tray. The detachable arrangement makes it possible to combine different trays T with different data memories 11.

The data memory 11 houses a control unit 3, a power source 4 and an input unit 5, and has a display 6 mounted thereon.

Figure 3C:
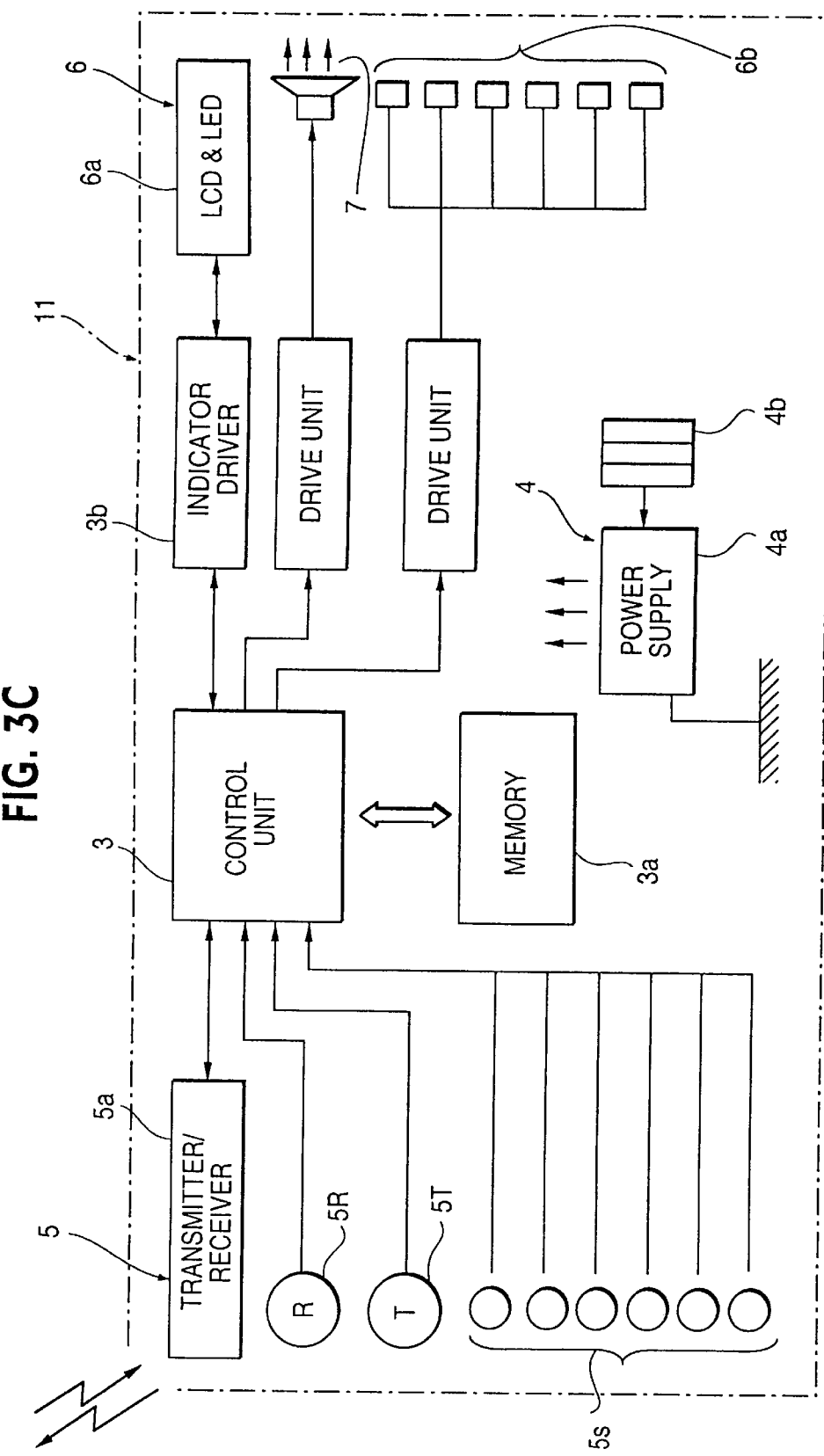
FIG. 3C is a block diagram of the memory of FIG. 3B.

FIG. 3C shows a block diagram of a control circuit in the data memory 11. The control circuit includes a memory 3a and a display driver 3b. The power source 4 comprises a battery 4a and a solar battery 4b. But one of the batteries may be omitted. The input unit 5 includes a signal transmit/receive unit 5a, drug type switches 5S, timer 5T and reset key 5R. The display 6 is a liquid crystal display.

Patients' names or codes are entered through the signal transmitter/receiver 5a attached to the side of the data memory 11. The unit 5a has an IDX which is a non-contact type IC card having a read/write IC memory. On command by a light signal from a light transmitter/receiver provided in a pharmacy, necessary data are written in or read from the IC memory. Instead of the IDX, the signal transmitter/receiver 5a may be of the type that utilizes radio waves or ultrasonic signals.

Respective drug type switches 5S are pressed every time tablets, powdered drugs or other drugs have been prepared. The liquid crystal display 6a can display all the prescription data.

The display 6 comprises the liquid crystal display 6a and six LED displays 6b for displaying the number of times each switch 5S has been pressed. The liquid crystal display 6a has a sufficient size and capacity to display all the necessary prescription data including patients' names or codes in letters, figures and characters. Numeral 7 is a loudspeaker.

A vast variety of medications are prescribed to each patient by doctors. Medications prescribed for each patient are classified into a plurality of groups such as tablets, powdered drugs, liquid drugs, and external drugs, and the drugs in the respective groups are prepared separately from each other. When the drugs in any group have been prepared, a pharmacist presses the corresponding switch 5S. The control unit records the time when a switch 5S is pressed.

Drugs are prepared in many different ways in different pharmacies. In some pharmacies, e.g. powdered drugs are prepared, packaged and put in bags fully automatically. In other pharmacies, they are manually prepared, packaged and put in bags.

When drugs for each patients have been prepared either automatically or manually, they are collected. Necessary drugs are put in each tray at the respective drug preparing stations. When all the necessary drugs in one group, e.g. tablets, have been prepared, the corresponding switch 5S is pressed. When all the switches are pressed, which means that all the necessary drugs for one patient have been prepared, the tray for this patient is carried to the inspection station.

The inspection table H is an ordinary table. A pharmacist inspects drugs in trays T on the table H. The table J at the drug delivery window is also a plain table on which are placed the input unit 1 (not shown) and the receiver 13. The receiver reads data stored in the data memories 11 of the trays T on command by light signals similar to light signals used for the transmitter 12.

The data processing unit 14, which is a personal computer similar to the host computer 2, temporarily stores data retrieved from the data memories 11 and processes them. The thus processed data are displayed on the display 15 (CRT). Patient data transmitted from the host computer 2 through a communication line (FIG. 2) are compared with the data retrieved from the data memories 11 of the trays T to check if they match.

Figure 4A:
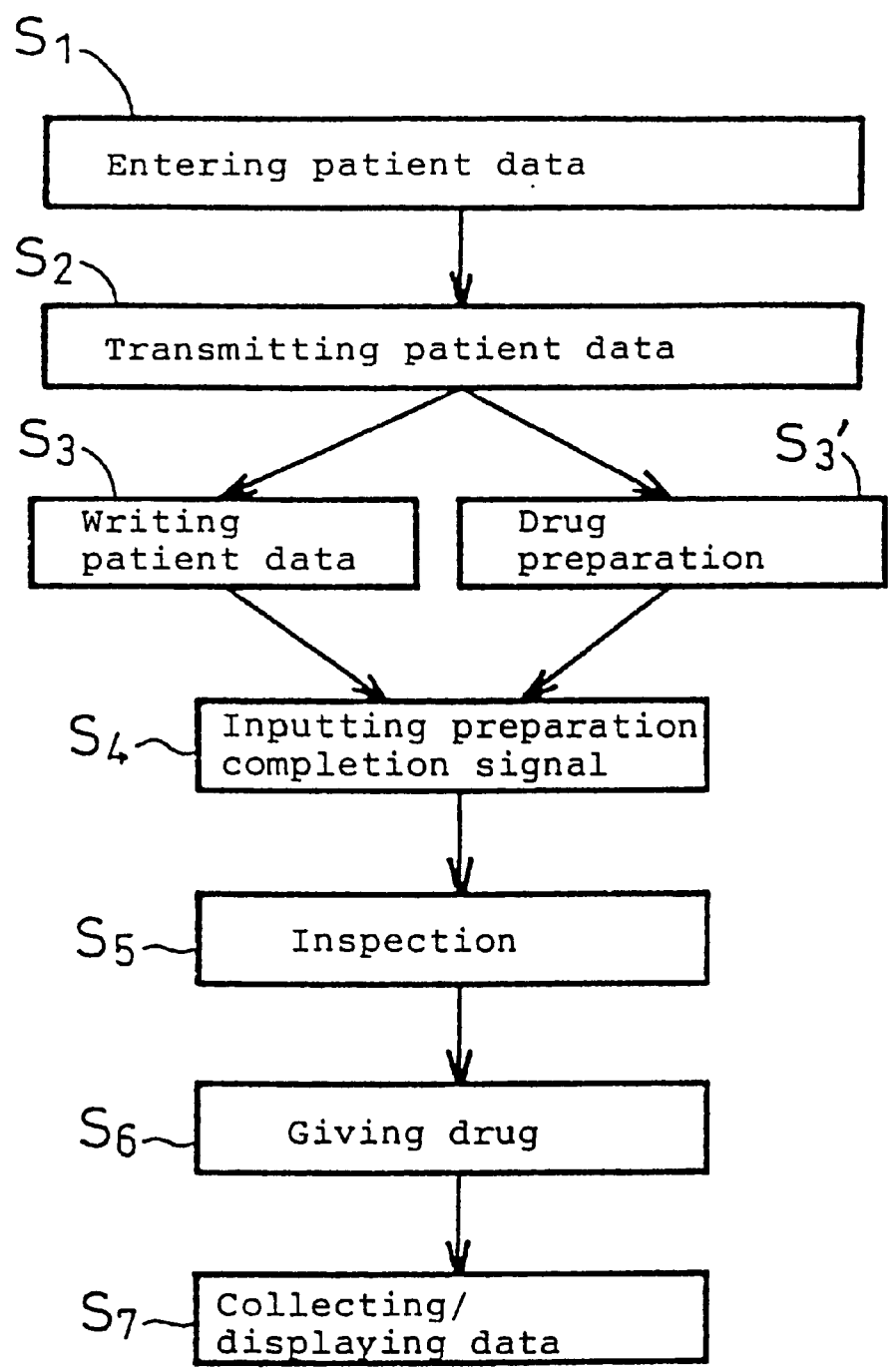
FIG. 4A schematically shows the flow of drug preparation.

Now the operation of this embodiment is described with reference to FIGS. 4A, 4B and 5. FIG. 4A generally shows processing steps.

As shown in FIG. 4A, prescription-based patient data such as patient numbers and names are entered into the host computer 2 through the input unit 1 provided at the prescription reception window (Step S1).

In Step S2, the data for each patient are transmitted to the necessary processing units of the drug processing unit 10, i.e. the units for preparing drugs needed for the patient (Step S3'). Simultaneously, the patient data is entered in a non-contact manner into the data memory 11 of a tray (Step S3).

These data are entered into the data memory 11 of a tray T sitting opposite the transmitter 12 in the area F. An exchange slip number, preparation data and the data entry time are also entered.

Simultaneously with or slightly after the data entry into each data memory 11, preparation for necessary drugs is started in the respective processing units. When all the necessary drugs have been prepared in each processing unit, this time is recorded in the memory 11 (Step S4). When all the drugs for one patient have been prepared, this time is also recorded in the memory 11.

In Step S5, the drugs in each tray are inspected. In Step S6, the tray is carried to the reception window for pickup by a patient. In Step S7, data are processed and displayed. For this purpose, data stored in the memory 11 of each tray are received by the receiver 13. Such data includes:
1. exchange slip number
2. data entry time
3. current time
4. preparation completion time in each processing unit
5. preparation completion time for all the drugs of one prescription
6. drug data The data signal including these data is transmitted through the receiver 13 to the data processing unit 14 for processing and analysis and then displayed on the display 15. The above is a general flow. Specifically, the data processing unit 14 calculates the total processing time taken to prepare drugs in each processing unit and the total time taken for inspection for every half hour of one day, and display the total processing time for every half-hour period in each processing unit and inspection station, as well as the waiting time, on the display 15. FIG. 4B is a schematic flowchart of such data processing, and FIG. 5 is its detailed flowchart. The flow of FIGS. 4B and 5 is logic controlled by a computer.

In Step SS1 (FIG. 4B), prescription completion data and processing data for every unit time period for a plurality of patients are retrieved from the memories of the corresponding trays by the receiver 13, transmitted to the data processing unit 14, and stored in the memory (not shown) of the unit 14. In Step SS2, the data for a respective drug kind for every unit time period (e.g. thirty minutes) except the inspection data are retrieved from all the data stored in this memory.

In Step SS3, the processing unit 14 calculates the total number of prescriptions processed in each drug processing unit and the processing time taken in each unit time period in Step SS3, and the total inspection time and the total processing time for all of the patients in each unit time period in Step SS4. The total inspection time is obtained by subtracting the total of the processing time periods in the respective drug processing units from the total processing time.

The processing unit also calculates the number of prescriptions received, the number of prescriptions issued, the number of prescriptions left unprocessed, maximum waiting time, average waiting time, and minimum waiting time. These data are displayed on the display 15 in Step SS5. Later, we will describe specifically what is shown on the display.

The processing unit continues such data processing work until the end of the working hour of the day. In Step SS6, the processing unit calculates weekly, monthly or yearly data at the end of the week, the month or the year by totaling the day-to-day data. In SS7, such weekly, monthly or yearly data are shown on the display.

Figure 4B:
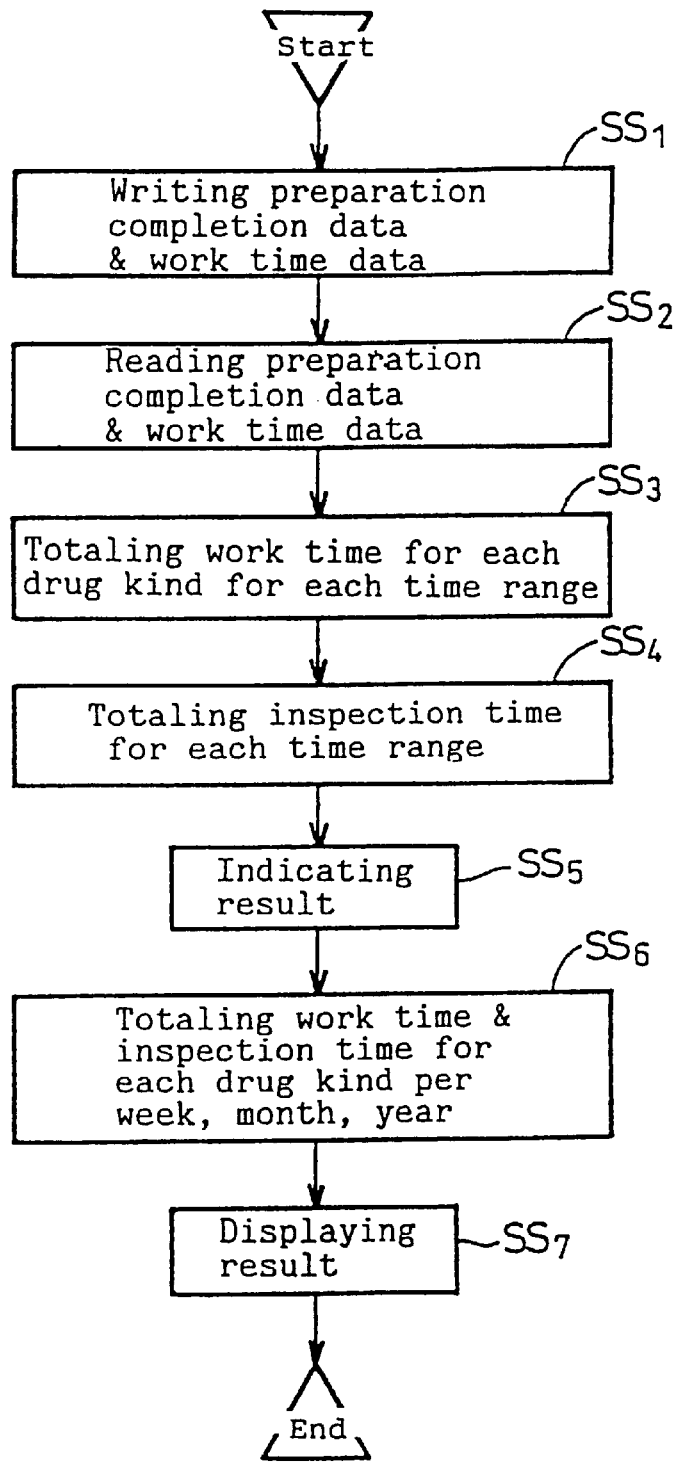
FIG. 4B schematically shows the flow in the data processing unit.
Figure 5:
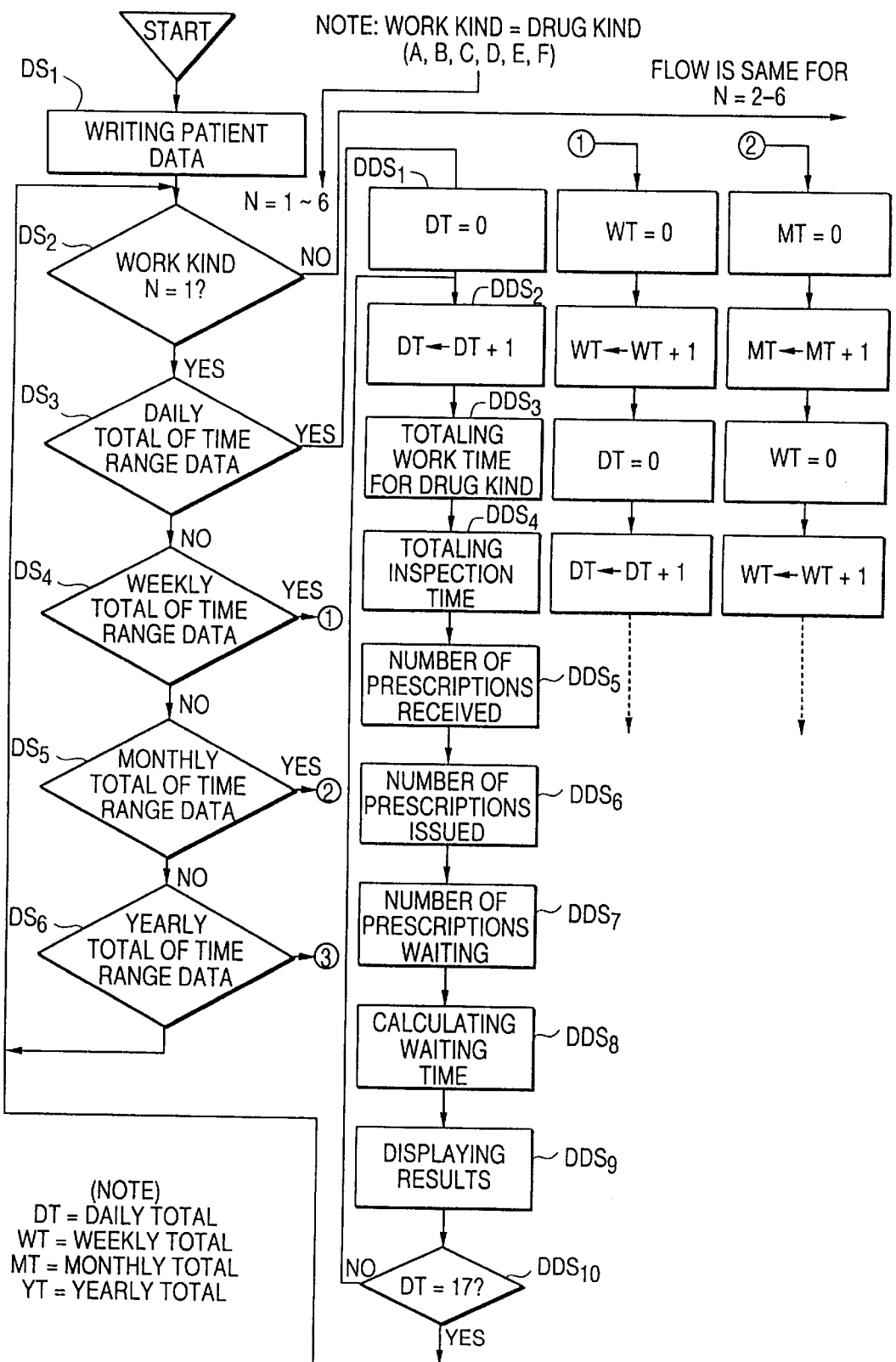
FIG. 5 is a detailed flowchart of the flow in the data processing unit.

The flow of FIG. 5 is now described except its portions overlapping with the flow of FIG. 4B. In Step DS1, data are written in a manner similar to Step SS1 of FIG. 4B. In Steps DS2–DS6, the kinds of processing (or kinds of drugs processed) and the time period for which the total processing time is calculated are judged, and the total processing time and inspection time for each kind of drugs are calculated.

When data for each type of processing, e.g. each drug group, are processed in each drug processing unit, the processing starting time and the processing completion time corresponding to each patient data are entered into the memory of a corresponding tray. When such data are processed, in DS2, the type of processing and the time period for which the totaling is carried out are judged. If N=1, in which N=1–6 corresponds to the respective drug processing units A–D and if the time period is a daily data division, the corresponding total processing time is calculated.

To calculate the total processing time for each time period, a variable T is changed e.g. from 1–17, in which T=1 is the time period from 8:30 to 8:59, T=2 is from 9:00 to 9:29. . . T=19 is from 16:30 to 16:59, and the data for each time period are called and totaled. The total processing time for each time period is given by subtracting the time taken for drug preparation from the total time period which is from the time when the drug preparation for a plurality of patients starts for each drug group for each time range until the thus prepared drugs are delivered to the drug pickup window (DDS4).

The total prescription number received (DDS5), the total number issued (DDS6), the total number remaining (DDS7), and the waiting time (DDS8) are calculated based on the patient data. The total number remaining is given by subtracting the total number issued from the total number received. The waiting time is given by totaling the time periods taken from the time when prescriptions for respective patients are received until their drugs are prepared and dividing the total time by the number of patients. The waiting time data are displayed in Step DDS9.

Such data, given for each drug group and for each time range, are combined to obtain data for all the drug types and the whole day. In FIG. 6, data are obtained for each variable N=1–6 in the above-described manner. The variable DT changes with the passage of time indicated by a clock in the data processing unit. Data for time periods yet to pass are not counted in for totaling.

Figure 7:
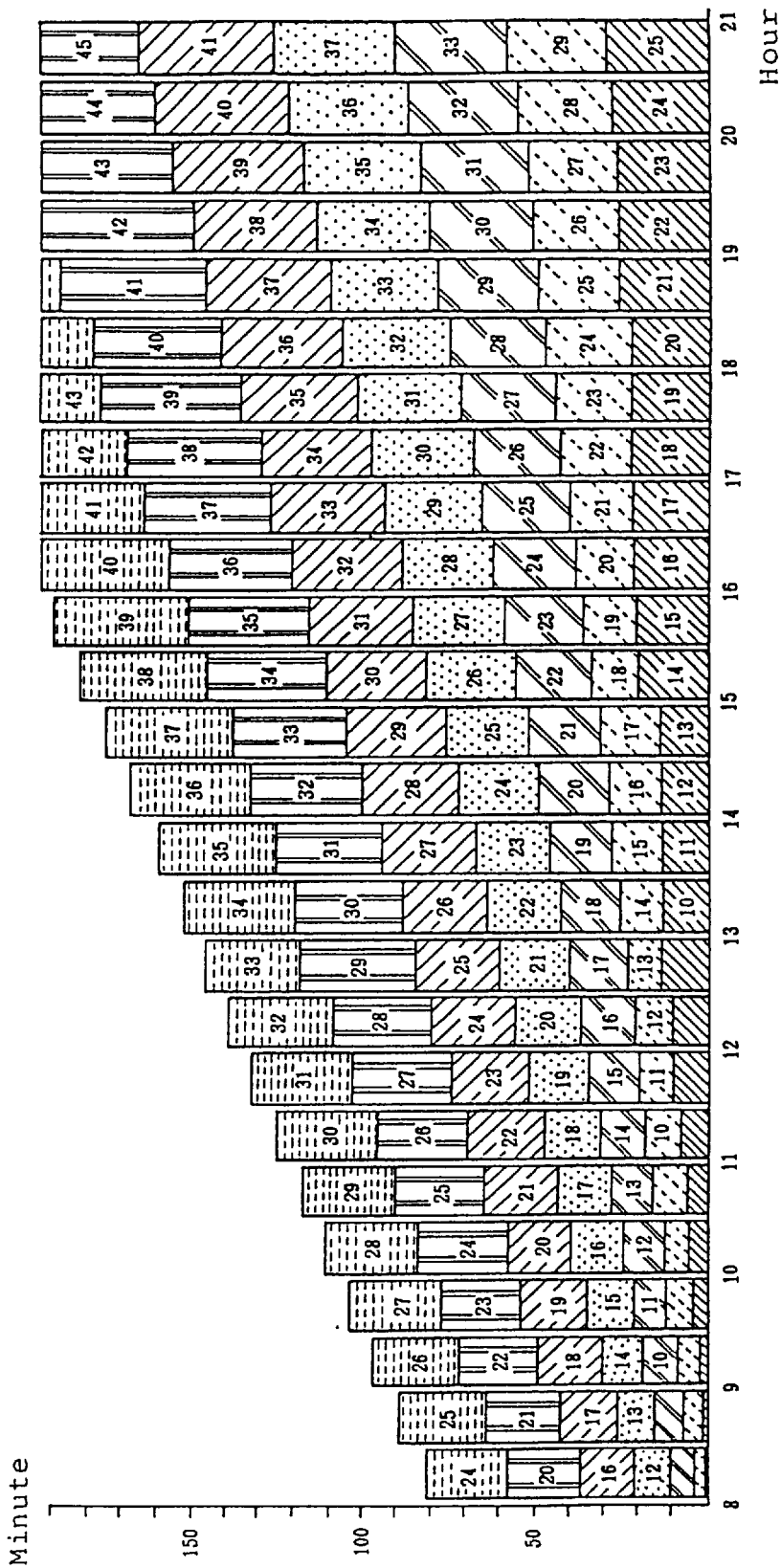
FIG. 7 is a standard pattern of a graph of displayed data.

These data are displayed selectively in one of two different ways, i.e. in the form of a data table shown in FIG. 6 and a graph shown in FIG. 7. The table in FIG. 6 shows in figures the total number of prescriptions received, maximum, average and minimum processing time periods, the total number of prescriptions issued, and the total number of prescriptions left unprocessed for each time range. The graph of FIG. 7 is a bar graph showing the number of prescriptions processed in each time range for each drug group, the total of the respective processing times, and the total of the entire processing times.

The graph of FIG. 7 shows the peak of the processing time for each drug group. Each bar of the graph in FIG. 7 shows the total of the processing times for the respective drug groups in each time range, and represents a standard (or reference) pattern, i.e. the average total time (and average total number of prescriptions processed) for each drug group in each time range.

Figure 8:
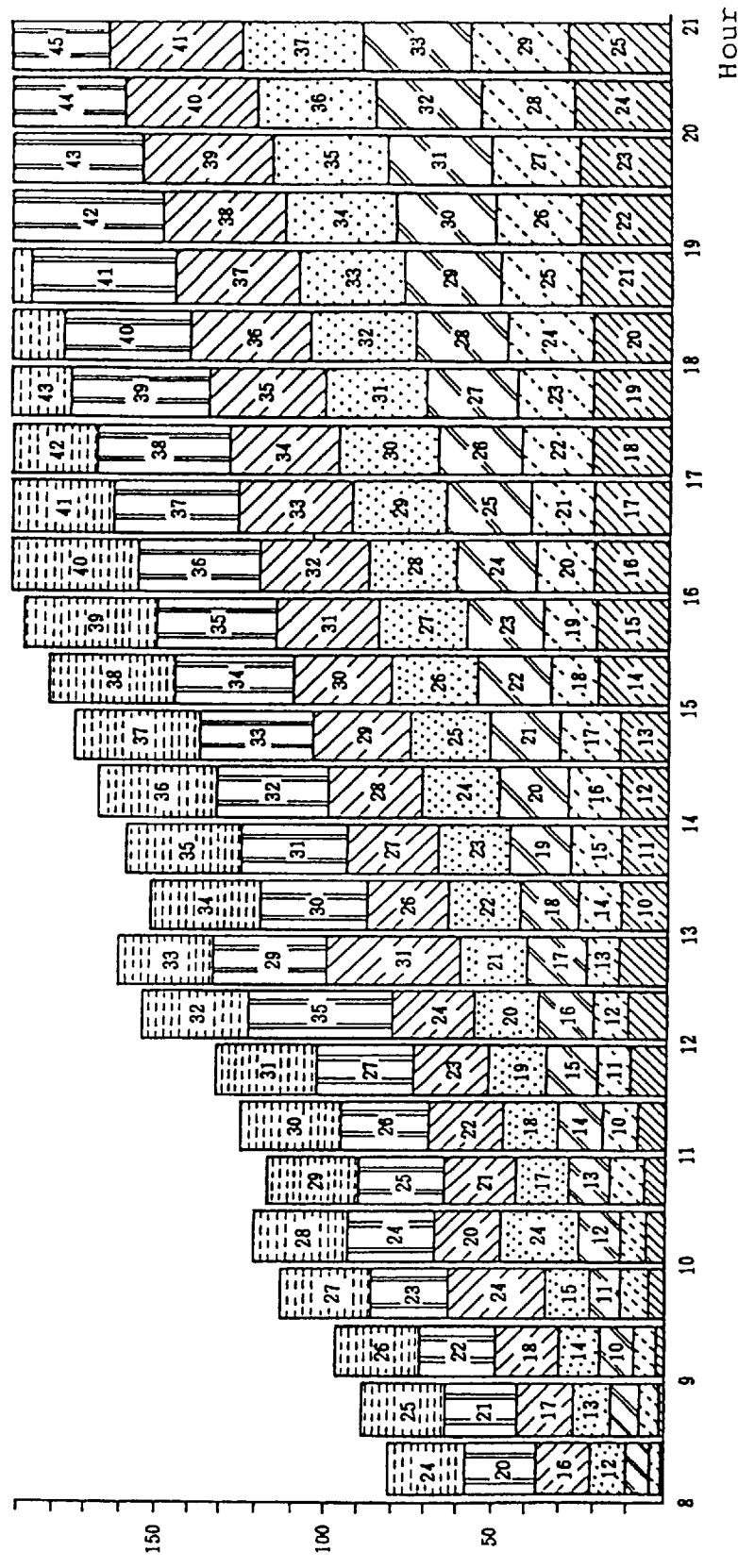
FIG. 8 is an example of an actual pattern of a graph of displayed data.

FIG. 8 is a graph showing the actual processing time distribution pattern in one day. As shown, longer times are taken to process drugs in certain groups in certain time ranges. For example, in the time period from 9:30 to 9:59 (T=4), five more prescriptions are processed for powdered drugs and 10 more minutes are taken to process powdered drugs than in the same time range in the standard pattern. Similarly, in the time range from 10:00 to 10:29 (T=5), the number of prescriptions processed is eight more and the processing time is 10 minutes longer for packed powdered drugs; in the time range from 12:00 to 12:29 (T=9), the number of prescriptions processed is seven more and the processing time is 15 minutes longer for packed tablet drugs; and in the time range from 12:30 to 12:59 (T=10), the number of prescriptions processed is six more and the processing time is 16 minutes longer for powdered drugs.

By comparing the processing time data for each time range in one day with the corresponding data in the standard pattern, it is possible to know which drug groups in which time ranges need longer times for preparation. The graphs shown in FIGS. 7 and 8 show the state at the end of the day. During the working hours of one day, only bars for the time ranges that have passed are shown. For example, at 13:00, only the bars before this time are shown.

Referring now back to the flowchart of FIG. 5, weekly, monthly or yearly total data are calculated. In the flows of ① and ② in FIG. 5, the weekly or monthly total data are calculated based on the entire data using variable WT (week) or MT (month). But instead, such data may be calculated using a totaling program. In the flow of ③, only the total of the total processing times for the respective time ranges is calculated (not shown).

FIG. 9 is a schematic block diagram of the drug processing system of the second embodiment. This embodiment differs from the first embodiment in that the trays T' have no memories. Thus, in this embodiment, every time drugs in one group are prepared, an input switch 11' of each processing unit is pressed to input a switch signal. The drug preparation completion data is thus transmitted to the data processing unit 14 on command of the host computer 2, together with the patient data and the data on the drug preparation starting time.

The data processing unit 14 has a switch 13'. Every time a tray T' carrying inspected drugs is delivered to a drug pickup window, the switch 13' is pressed to indicate that all the drugs for one patient has been prepared.

In the second embodiment, in which are used trays T' having no memories, the process in the first embodiment for entering the data stored in the memory of each tray T into the data processing unit 14 on the work completion signal when the tray T is delivered to the drug pickup window G is carried out by data communication among the host computer, drug processing units 10 and data processing unit 14, in basically the same manner and procedure as the first embodiment.

In either of the first and second embodiments, data on drug preparation completion time is entered manually by pressing the switch on each tray having a memory or the switch on each drug processing unit. But instead, if, for example, the tablet processing unit is a fully automatic type, the tablet preparation completion signal may be produced therein and automatically transmitted from the tablet processing unit to the data processing unit 14.

As has been described in detail, the drug preparation processing system according to this invention has a plurality of drug processing units and a control unit provided in combination with the drug processing units. The control unit gathers time data and patient data and calculates the total processing time for each time period. The thus processed data is displayed. By comparing the total processing time with the standard data, a pharmacy superviser can instantly see which processing or inspection station or stations are busy in which time period or periods. Thus, he can distribute pharmacy personnel into the respective processing and inspection stations in an optimum way.

What is claimed is:

1. A medication processing system comprising:
    a carrier storage area for temporarily storing drug carriers;
    a plurality of drug processing units for preparing medications according to data indicated on prescriptions including the kinds and quantity of medications and patient names or codes,
        said drug processing units being provided in the vicinity said carrier storage area;
    a drug inspection station for receiving medications prepared according to data indicated on the prescriptions; and
    a control unit for storing data on drug preparation starting times, completion times and processing times in said respective drug processing units and in said drug inspection station, and for calculating the total processing time in each of said drug processing units and said drug inspection station during each specified time range, and for each kind of drug.

2. A medication processing system as claimed in claim 1, wherein said control unit further calculates a total number of prescriptions processed in each of said drug processing units and said drug inspection station for each time range.

3. A medication processing system as claimed in claim 2, wherein said control unit is capable of further calculating the average processing time and the number of prescriptions that are unprocessed based on said drug preparation starting and completion times and said patient data, for each specified time range.

4. A medication processing system as claimed in claim 2, further comprising a transmitter, provided on said carrier storage area, for transmitting data to a memory provided on each of the carriers,
    wherein patient data including the drug preparation starting and completion times in said respective drug processing units and the kinds of drugs are transmitted by said transmitter in order to store said data in the memory of each of the carriers through a receiver of the memory, and said data stored in the memory being transmitted to said control unit each time one of said carriers is moved to a drug pickup window.

5. A medication processing system as claimed in claim 2, wherein time data includes the drug preparation starting and completion times in each of said drug processing units,
    wherein the drug preparation completion times are entered by pressing a switch provided at each of said drug processing units, and stored in said respective drug processing unit, together with patient data including the drug types, and wherein the stored data are transferred to said control unit, and when each of said carriers reaches a drug pickup window, the drug preparation completion times are inputted by means of a switch provided at said control unit.

6. A medication processing system as claimed in claim 2, wherein said control unit includes a display means for displaying data collected or calculated.

7. A medication processing system as claimed in claim 1, wherein said control unit is capable of further calculating the average processing time and the number of prescriptions that are unprocessed based on said drug preparation starting and completion times and said patient data, for each specified time range.

8. A medication processing system as claimed in claim 7, further comprising a transmitter, provided on said carrier storage area, for transmitting data to a memory provided on each of the carriers, wherein patient data including the drug preparation starting and completion times in said respective drug processing units and the kinds of drugs are transmitted by said transmitter in order to store said data in the memory of each of the carriers through a receiver of the memory, and said data stored in the memory being transmitted to said control unit each time one of said carriers is moved to a drug pickup window.

9. A medication processing system as claimed in claim 7, wherein time data includes the drug preparation starting and completion times in each of said drug processing units, wherein the drug preparation completion times are entered by pressing a switch provided at each of said drug processing units, and stored in said respective drug processing unit, together with patient data including the drug types, and wherein the stored data are transferred to said control unit, and when each of the carriers reaches a drug pickup window, the drug preparation completion times are inputted by means of a switch provided at said control unit.

10. A medication processing system as claimed in claim 7, wherein said control unit includes a display means for displaying data collected or calculated.

11. A medication processing system as claimed in claim 1, further comprising a transmitter, provided on said carrier storage area, for transmitting data to a memory provided on each of the carriers, wherein patient data including the drug preparation starting and completion times in said respective drug processing units and the kinds of drugs are transmitted by said transmitter in order to store said data in the memory of each of the carriers through a receiver of the memory, and said data stored in the memory being transmitted to said control unit each time one of the carriers is moved to a drug pickup window.

12. A medication processing system as claimed in claim 11, wherein said control unit includes a display means for displaying data collected or calculated.

13. A medication processing system as claimed in claim 1, wherein time data includes the drug preparation starting and completion times in each of said drug processing units, wherein the drug preparation completion times are entered by pressing a switch provided at each of said drug processing units, and stored in said respective drug processing unit, together with patient data including the drug types, and wherein the stored data are transferred to said control unit, and when each of said carriers reaches a drug pickup window, the drug preparation completion times are inputted by means of a switch provided at said control unit.

14. A medication processing system as claimed in claim 13, wherein said control unit includes a display means for displaying data collected or calculated.

15. A medication processing system as claimed in claim 1, wherein said control unit includes a display means for displaying data collected or calculated.

16. A medication processing system as claimed in claim 15, wherein said display means can display the data processed by said control unit in the form of a graph.

* * * * *